United States Patent
Hasson et al.

(10) Patent No.: US 7,239,988 B2
(45) Date of Patent: Jul. 3, 2007

(54) APPARATUS AND METHOD FOR EFFICIENT REPRESENTATION OF PERIODIC AND NEARLY PERIODIC SIGNALS FOR ANALYSIS

(75) Inventors: Assaf Hasson, Tel Aviv (IL); Amir Beker, Rosh Ha'ayin (IL); Tamir Ben-David, Tel Aviv (IL)

(73) Assignee: BSP Biological Signal Processing Ltd., Tel-Aviv (IL)

( * ) Notice: Subject to any disclaimer, the term of this patent is extended or adjusted under 35 U.S.C. 154(b) by 491 days.

(21) Appl. No.: 10/469,994

(22) PCT Filed: Mar. 19, 2002

(86) PCT No.: PCT/IL02/00222

§ 371 (c)(1),
(2), (4) Date: Sep. 16, 2003

(87) PCT Pub. No.: WO02/075584

PCT Pub. Date: Sep. 26, 2002

(65) Prior Publication Data

US 2004/0093192 A1    May 13, 2004

Related U.S. Application Data

(60) Provisional application No. 60/276,481, filed on Mar. 19, 2001.

(51) Int. Cl.
   *G06F 17/10*  (2006.01)
(52) U.S. Cl. .......................... 703/2; 600/523
(58) Field of Classification Search .................. 703/21, 703/22, 2; 600/509, 517, 521, 523
   See application file for complete search history.

(56) References Cited

U.S. PATENT DOCUMENTS

| | | | |
|---|---|---|---|
| RE35,122 E * | 12/1995 | Corenman et al. | 600/324 |
| 5,545,976 A * | 8/1996 | Cutler | 324/76.38 |
| 5,622,178 A | 4/1997 | Gilham | |
| 5,938,594 A * | 8/1999 | Poon et al. | 600/300 |
| 5,956,013 A | 9/1999 | Raj et al. | |
| 6,001,065 A | 12/1999 | DeVito | |
| 6,201,985 B1 * | 3/2001 | Polzin et al. | 600/411 |
| 6,654,623 B1 * | 11/2003 | Kastle | 600/336 |
| 2004/0093192 A1 | 5/2004 | Hasson et al. | |

FOREIGN PATENT DOCUMENTS

WO   PCT WO 02/075584      9/2002

* cited by examiner

*Primary Examiner*—Albert W. Paladini (57) ABSTRACT

Apparatus for graphically representing a substantially periodic signal having substantially periodic segments, comprising a graphic transformer for converting the periodic segments into encodings respectively for arrangement in a first dimension and successively indexing the encodings to form a two-dimensional coded image, thereby to represent, within the image, dynamic changes of the periodic segments over the signal.

67 Claims, 5 Drawing Sheets

(2 of 5 Drawing Sheet(s) Filed in Color)

APPARATUS AND METHOD FOR EFFICIENT REPRESENTATION OF PERIODIC AND NEARLY PERIODIC SIGNALS FOR ANALYSIS

RELATED PATENT APPLICATION

This application is a National Phase Application of PCT/IL02/00222 International Filing Date 19 Mar. 2002, which claims priority from U.S. Provisional Patent Application Ser. No. 60/276,481 filed 19 Mar. 2001.

FIELD AND BACKGROUND OF THE INVENTION

The present invention relates to an apparatus and method for efficient representation of periodic and nearly periodic signals for analysis.

Analysis of periodic or nearly periodic signals does not, as a rule, rely solely on an inspection of single periods themselves. In many cases, inspection of an evolution of changes in a periodic part of a signal over time may reveal important information. However, in relatively long signals (containing a large amount of periods) a standard continuous representation of the signal makes inspection of the signal (i.e. the entire data) a tedious and ineffective task, especially if signal changes are gradual and moderate. One specific example of this problem is found in electrocardiogram (ECG) analysis of the human heart.

An ECG describes the electrical activity of the heart's muscle, which initiates and accompanies its mechanical activity. An ECG signal is recorded by body surface electrodes that measure the change in electrical potentials over the body due to the propagating electrical activation in the heart. Visual inspection of the ECG signal is the basic and most common non-invasive means for detection and diagnosis of cardiac abnormalities. The main features forming the basis for ECG diagnosis, which give indication of gross morphological changes, are: the P wave, describing the depolarization of the atria; the QRS complex, describing ventricles depolarization; and the T wave, describing ventricle repolarization.

Thus, extraction of information related to heart activity by means of ECG inspection and analysis concentrates on what is known as the P-QRS-T segment of the signal. However, analysis typically ignores large portions of the ECG signal—those portions corresponding to periods between any two consecutive heart beats. With the exception of the identification and interpretation of cardiac arrhythmias, most of the commonly used diagnostic aids based on ECG data, such as an S-T segment shift, prolonged and bizarre QRS complex patterns, or T wave inversion are—as indicated by their names—related primarily to inspection of the P-QRS-T segment of the signal.

The significant frequency range of ECG signals is traditionally considered to be from 0.05–100 Hz. Although all common diagnostic methods mentioned above are based solely on information contained in the 0.05–100 HZ frequency range, valuable information is known to be found in higher frequencies. Abboud et al ("High-Frequency Electrocardiogram Analysis of the Entire QRS in the Diagnosis and Assessment of Coronary Artery Disease", Progress in Cardiovascular Diseases, Vol. XXXV, No. 5, March/April 1993), the contents of which are hereby incorporated by reference, have shown in a series of studies a correlation between significant decrease in the high frequency (HF), namely 150–250 Hz, content of the QRS signal and an ischemic condition of the heart.

In both traditional ECG based diagnosis methods and in more recent HF ECG based methods, it is common that cardiac abnormalities (ischemia being the most important) which are not present at rest, may be manifested during physiological stress, usually caused by exercise. Thus, comparison of an ECG signal of a subject under physiological stress with the same subject's ECG signals at rest and during a recovery period is commonly used for detection and identification of cardiac abnormalities. It should be noted, however, that existing continuous representations of the ECG signal do not allow easy inspection of the evolution of a signal during a test—the test being typically 10–20 minutes long, thus involving many hundreds of heart beats.

While standard ECG diagnosis methods may be (and actually are) based on local data, the situation in HF ECG methods is a more delicate one: as signal to noise ratio is far worse in the HF range than in the standard 0.05–100 HZ range, accuracy of local data in the HF portion of a signal might not be sufficient. Therefore, whereas a global representation of a standard ECG signal of a complete exercise test may be viewed as a diagnostic aid, serving as an improvement upon traditional ECG analysis methods, it is of utmost importance in the diagnosis and interpretation of HF ECG signals.

Further studies by Beker et al ("Analysis of High Frequency QRS Potential during Exercise Testing Patients with Coronary Artery Disease and in Healthy Subjects", Biomedical Engineering Department, Faculty of Engineering, Tel-Aviv University, 1995), the contents of which are hereby incorporated by reference, showed that a decrease of the HF ECG of a QRS complex during exercise test could serve as an indication for early detection of ischemic pathologies. These findings make inspection of an HF ECG highly interesting, and call for development of tools that may tackle problems such an inspection imposes. An HF ECG signal has a significantly lower amplitude than a standard ECG, and therefore an HF ECG cannot be usefully dealt with, without first improving its signal to noise ratio.

The results presented by Beker et al. are based on a comparison of the HF ECG signal at rest with the same signal during exercise. However, the HF ECG signal is susceptible to drastic and sudden changes that are not necessarily due to an ischemic condition of the heart, but rather to outer changes such as the patient's body position. Any diagnostic tool based on HF ECG will have to differentiate between these sudden changes and the changes in the signal caused by ischemia.

It is clear from the discussion above that a local inspection of the HF ECG signal is prone to errors for the following reasons:

It seems impossible to reduce the level of noise to a completely insignificant one, without distorting the HF ECG signal itself. Thus some level of noise will always occur in the signal, and its overall effect should be evaluated over a relatively long timescale.

It seem impossible to determine, by inspecting the HF level of two different QRS complexes, whether the difference between these signals is due to ischemia or to an artifact caused by a movement of the patient.

SUMMARY OF THE INVENTION

According to a first aspect of the present invention there is thus provided an apparatus for graphically representing a substantially periodic signal having substantially periodic segments, the apparatus comprising a graphic transformer for converting said periodic segments into encodings respectively for arrangement in a first dimension and successively indexing said encodings to form a two-dimensional coded image, thereby to represent, within said image, dynamic changes of said periodic segments over said signal.

Preferably, a period identifier, associated with said graphic transformer, identifies a period of said signal, thereby to enable segmentation of said signal into said periodic segments.

Preferably said period identifier comprises a time-oriented aligner and a morphology-oriented aligner to allow substantial alignment of said periodic segments.

Preferably said time oriented aligner is operable to effect said alignment by defining a reference point in each of a plurality of said periodic segments.

Preferably said morphology oriented aligner is operable to effect said alignment against a segment template.

Preferably said segment template is at least one chosen from a list comprising: a set of local maxima and minima of said periodic segment, a characteristic overall shape of said periodic segment, and a characteristic portion of said periodic segment.

Preferably said time-orientated aligner and said morphology-oriented aligner are operable together to effect alignment of said periodic segments.

Preferably said time-orientated aligner is operable to effect alignment of said periodic segments.

Preferably said morphology-orientated aligner is operable to effect alignment of said periodic segments.

Preferably said periodic segment comprises a complex of features and said graphic transformer is associated with a feature encoder for encoding a feature of said periodic segment into said encoding.

Preferably said encoding comprises a color scale used against a relative position within said period, thereby to form said encoding as a continuous colored line representing said feature at respective positions of said periodic segment.

Preferably said encoding comprises a gray scale used against a relative position within said period, thereby to form said encoding as a continuous gray scale line representing said at least one feature at respective positions of said period.

Preferably said encoding comprises a gray scale used against a relative position within said period, thereby to form said encoding as a continuous gray scale contour map.

Preferably said graphic transformer further comprises a segment smoother operable in association with said feature encoder to effect smoothing of data within said periodic segment.

Preferably said feature is amplitude.

Preferably said segment smoother comprises an interpolation filter and a signal data reducer.

Preferably said interpolation filter is operable to selectively interpolate data of regions of respective periodic segments to enable a smooth representation of said data.

Preferably said signal data reducer is operable to selectively reduce data of regions of respective periodic segments to enable a smooth representation of said data.

Preferably said signal is a biological signal.

Preferably said signal is an ECG signal.

Preferably said ECG signal is at least one of a group comprising an exercise ECG test signal and a rest ECG signal.

Preferably said ECG signal is a Holter recording signal.

Preferably said period identifier is operable to use selected frequency band components to carry out said alignment.

Preferably said period identifier is further operable to use said selected frequency band components to improve said alignment.

Preferably said period identifier further comprises:
a noise reducer operable to reduce noise in said aligned periodic segments,
a filter for selected frequency components, said filter operable upon said aligned periodic segments following noise reduction, and
a matrix orderer operable to order said aligned periodic segments in chronological order, following said frequency filtering.

Preferably said signal is an ECG signal.

Preferably said period identifier further comprises:
a period averager, usable in association with said time-oriented aligner and said morphology-oriented aligner to provide averaging over said period segments,
a template filter for filtering over said period segments, and
an array filter for filtering over an array of segments, to further improve said alignment.

Preferably said period averager is operable to average respective periods by averaging a predetermined number of consecutive periods in said array of periodic segments having a substantially low level of noise in a frequency band of interest to create a lower noise array of periodic segments.

Preferably said template filter is operable in association with said period averager, so that said lower noise array of periodic segments is selected frequency filterable to create a template array of periodic segments.

Preferably said array filter is operable in association with said time-oriented aligner and said morphology-oriented aligner by selected frequency filtering said array of periodic segments to create a filtered array of periodic segments.

Preferably said filtered array of period segments is realignable using said template array of periodic segments as a segment template.

According to a second aspect of the present invention there is thus provided an electronic graphic representation of a periodic or semi-periodic signal, comprising:
a first dimension representing properties for a periodic segment of said signal, and
a second dimension representing successive segments, thereby to form a two-dimensional coded image representative of dynamic changes within the periodicity of said signal.

Preferably said properties comprise a feature of said periodic segment.

Preferably comprising visual encoding of said feature.

Preferably comprising visual encoding of derived properties of said feature.

Preferably said visual encoding comprises a gray scale.

Preferably said visual encoding comprises a color scale.

Preferably said periodic signal is a biological signal.

Preferably said periodic signal is an ECG signal.

According to a third aspect of the present invention there is provided a method of representing a substantially periodic signal having substantially periodic segments to show dynamic changes in the periodicity of a signal, the method comprising transforming said periodic segments into encodings respectively for arrangement in a first dimension and successively indexing said encodings to form a two-dimensional coded image, thereby to represent, within said image, dynamic changes of said periodic segments over said signal.

Preferably the method further comprises identifying a period of said signal, thereby to enable segmentation of said signal into said periodic segments.

Preferably identification of said period of said signal further comprises the steps of:
aligning said periodic segments according to at least-one chosen from a list of time orientation and morphology orientation; and
reducing noise in said aligned periodic segments;

Preferably said period identification is performed using selected frequency band components to carry out said alignment.

Preferably said period identification further comprises the steps of:

filtering a selected frequency band from said noise-reduced aligned periodic segments; and ordering said filtered periodic segments in a matrix in chronological order.

Preferably said period identification uses said selected frequency band components to improve said aligning of said periodic segments.

Preferably said signal is a biological signal.

Preferably said signal is an ECG signal.

Preferably said ECG signal is obtained during at least one chosen from a list comprising exercise ECG tests and rest ECG tests.

Preferably signal ECG is obtained during a Holter recording.

Preferably at least one of a list comprising identifying and transforming, takes place in a personal digital assistant-like device.

Preferably at least one of a list comprising identifying and transforming, takes place in a portable ECG device.

Preferably further comprising manipulating said two-dimensional image graphically.

Preferably said manipulation comprises at least one chosen from a list comprising zoom in and zoom out.

Preferably said two-dimensional coded image is decodable to yield a representation of said segmented periodic segments.

Preferably said substantially periodic signal comprises a set of signals collected from at least two non-continuous signal portions.

Preferably said set of signals comprises a plurality of records spanning a period of an order of magnitude within a range of seconds to years, and more specifically in the ranges of tens of minutes to tens of hours.

Preferably said signal is a record of a biological signal comprising at least one chosen from a list comprising: EEG signals and ECG signals, wherein said signal is correlated to a series of repetitive external stimuli.

According to a fourth aspect of the present invention there is thus provided a method of representing a non-periodic signal containing a plurality of recurring signal segments to show dynamic changes in said signal segments, the method comprising transforming said signal segments into encodings respectively for arrangement in a first dimension and successively indexing said encodings to form a two-dimensional coded image, thereby to represent, within said image, dynamic changes of said signal segments over said signal.

Preferably the method comprises identifying said signal segments. Alternatively it may work on previously identified signal segments.

BRIEF DESCRIPTION OF THE DRAWINGS

The file of this patent contains at least one drawing executed in color photograph. Copies of this patent with color photograh(s) will be provided by the Patent and Trademark Office upon request and payment of necessary fee.

For a better understanding of the invention and to show how the same may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DESCRIPTION OF THE PREFERRED EMBODIMENTS

Preferred embodiments of the present invention comprise an apparatus and method for a two-dimensional representation of transformed one-dimensional periodic and nearly periodic signals. Transformation of the periodic part of the initial signal over time is indicated as one of the axes of the two-dimensional representation. Preferred embodiments are applicable to any signal in which most of the relevant information is concentrated in a distinct set of relatively short time-intervals containing morphologically close signal segments.

The embodiments are preferably applied, but not exclusively, to biological periodic signals as exemplified by human ECG signals. Preferred embodiments of the present invention include:

a. Identification and extraction of all occurrences of the periodic part of a signal to be analyzed, thereby creating a set of periodic segments.

b. Alignment of the set of periodic segments to allow comparisons across selected parts of each of the set of periodic segments.

c. Representation of the aligned set of periodic segments in a two dimensional format to enable and enhance analysis.

Further preferred embodiments of the present invention include an apparatus and method for representation of both standard and High Frequency (HF) ECG signals, providing a global view of the significant information in an ECG signal of many hundreds of heartbeats at a time. The preferred embodiments provide a tool for analysis of an ECG signal and, more particularly, a means to detect transient changes in a P-QRS-T segment during exercise or any other time dependent test.

Before explaining the embodiments of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1:
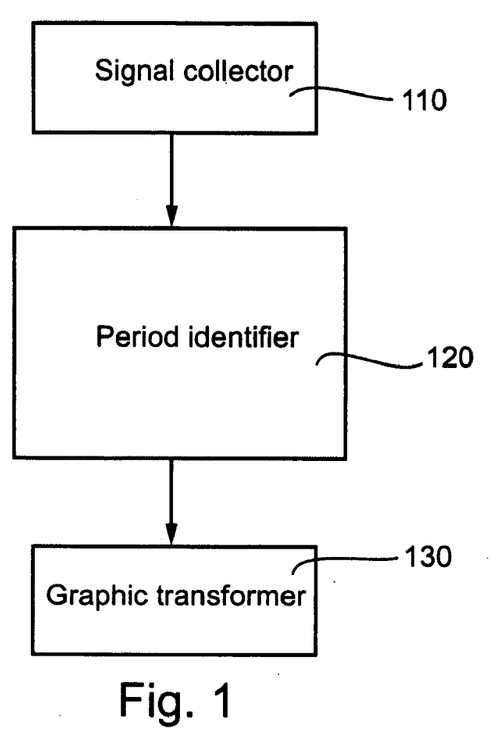
FIG. 1 is a simplified block diagram indicating the salient elements of an apparatus for efficient representation of periodic and nearly periodic signals for analysis, in accordance with a first preferred embodiment of the present invention.

Reference is now made to FIG. 1 which is a simplified block diagram indicating the salient elements of an apparatus for efficient representation of periodic and nearly periodic signals for analysis, in accordance with a first preferred embodiment of the present invention. In the present discussion, "signal" is used to refer to the entire data collected, and "segment" is used to indicate an arbitrary part of the signal (usually, but not necessarily, a continuous part of the signal). The apparatus described in FIG. 1 may be applied to any signal with periodic or nearly periodic behavior, enabling a 2-dimensional representation of 1-dimensional signals, adding to the presentation information related to the evolution of changes in the periodic part of the signal with time.

A signal collector 110 provides input to the system. This element is further discussed below. The signal is then transferred to a period identifier 120 which operates on a given segment of the signal, which is typically the entire signal but may be a portion of it, and defines periods for the signal segment. As a continuation of processing within period identifier 120, periods are then aligned with one another based on one or more criteria further described below. Aligned periods, also referred to as aligned events, are then transferred to a graphic transformer 130 where, according to one or more criteria, the periods are transformed into a 2-D presentation, so that periods are represented on one axis of a 2-D presentation with the second axis representing the succession of periods.

A particular example of a signal with periodic or nearly periodic behavior is an electrocardiogram (ECG). In this case, signal collection 110 is performed by body surface electrodes that measure a change in electrical potentials over a patient's body due to propagating electrical activation in the heart, for example, during an exercise test. Identification of periodicity 120 (or creation of a set of events) depends highly on the signal to be investigated and on the type of analysis it will be subject to. For instance, detection of prolonged QRS complexes in an ECG signal during exercise can be done using well-known algorithms to first detect and extract all the QRS complexes in the signal and then to identify the onset and the offset of each of the QRS complexes.

While identification of periodicity 120 in biological signals is a common and largely practiced procedure, aligning a set of events is a much less familiar procedure that plays a key role in ordering data to enable a comparative two-dimensional representation. Only a robust alignment algorithm can assure a meaningful comparison between two distant segments of a biological (and characteristically relatively unstable) signal. Alignment algorithms depend on parameters of an inspected signal. For that reason it is difficult to imagine a general alignment procedure that may cope with any given set of events. Furthermore, it should be stressed that, in general, alignment of a set of events would not automatically emerge as a by-product of the creation of that set. This point is true not only for delicate signals, such as HF ECG, which will be discussed below, but also for more robust signals, such as a standard ECG.

Figure 2:
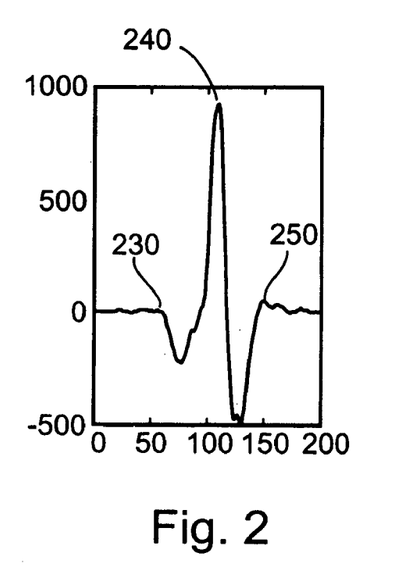
FIG. 2 is a schematic diagram of one typical QRS complex in an ECG signal.

Reference is now made to FIG. 2 which is a schematic diagram of one typical QRS complex in an ECG signal. A horizontal axis 210 represents time, in units of 1 msec. A vertical axis 220 represents amplitude in mV. A shape of a QRS wave is typified by various points such as: QRS onset 230; R-wave peak 240; and QRS offset 250. Those skilled in the art will note that FIG. 2 represents one of many such complexes present in a signal collected from an ECG, and that the exact shape of such a complex may vary significantly. The QRS complex shown in FIG. 2 is referred to below and in further discussion.

Regardless of a specific implementation of an alignment algorithm, two different approaches to the alignment problem are considered:

time oriented alignment: detecting a single reference point in each event, for example, onset 230 or offset 250 points of each event, and then aligning all events according to that set of points (for example, fixing a zero point of each event at a chosen reference point); and morphology oriented alignment: for all events, find an alignment that best approximates a given template, for example, min RMS of a difference signal or max cross-correlation. Obviously, the morphology oriented alignment method does not have to take into account all existing data for each event, and the morphology oriented alignment method may be effected using any partial information, such as a set of local maxima and minima of each event.

Clearly, the choice of an alignment method depends mostly on the signal and data to be extracted. In many cases a combination of the two methods, such as a time oriented first approximation, refined by a morphologically oriented alignment, will be needed.

A major aspect of the graphic transformer 140 of FIG. 1 is its presentation of an aligned set of events as a two-dimensional matrix, where every column corresponds to a single event, or to a time-averaged grouping of events. (The following discussion is equally valid for considering every row as a single event, in which case, the nomenclature for horizontal and vertical noted below would be reversed.) Thus, both directions of the matrix may be seen as representing a time variable. The vertical direction represents a shorter time interval corresponding to a duration of a single event (time-averaged grouping of events). A specific example of a single event would be one heartbeat period, typically on the order of under one second. In the case of a time-averaged grouping of events, each grouping could be on the order of 10 seconds. Note that the actual length of each such event also depends on the signal sampling rate. The horizontal axis represents a larger time interval corresponding to a length of the whole signal. The actual length of the segment depends only on the size of the set of events. A specific example of a length of the segment would be on the order of 20 minutes—a typical time for a stress test.

Alignment of the set of events allows viewing each row of the matrix as a set of corresponding points in an array of recurring events. Changes along a row of the matrix correspond to changes in recurring events. Graphical representation of the matrix therefore is a useful tool for emphasizing and efficiently detecting changes in recurring events.

To simplify notation henceforth, it is assumed that each column of the matrix represents a single period and that the rows of the matrix correspond to the evolution of the period with time. As previously mentioned, this assumption does not in any way constrain the alignment method and subsequent algorithms.

Figure 3:
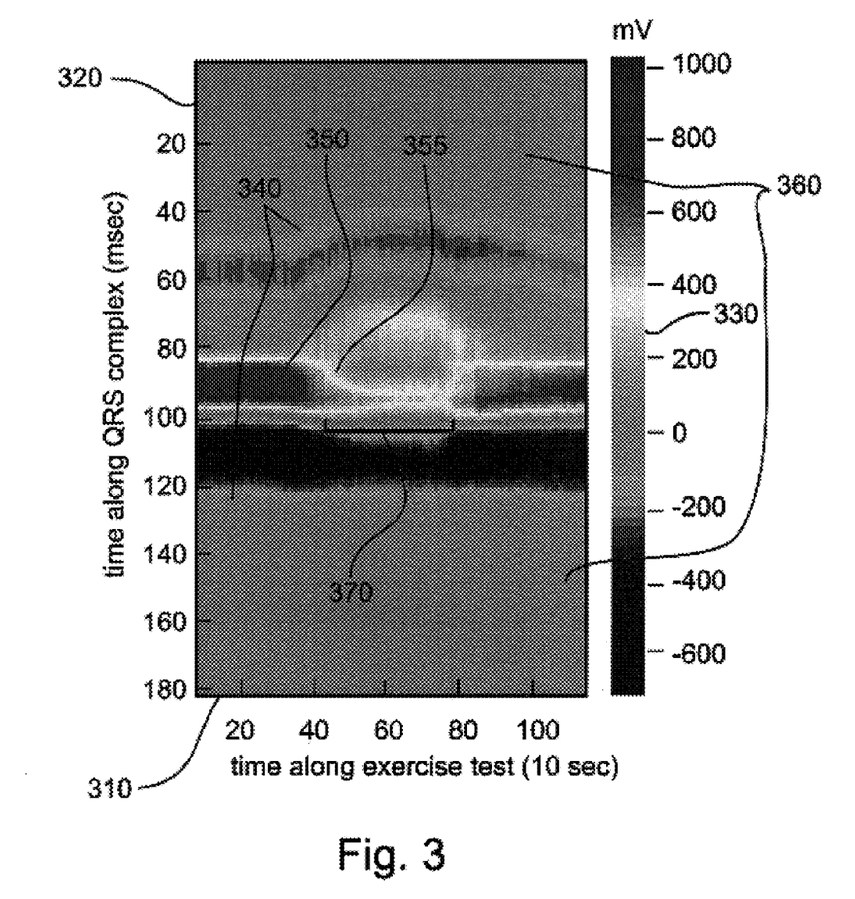
FIG. 3 is a graphical representation of a two-dimensional matrix, corresponding to electrical potential levels of QRS complexes of a patient during an 18-minute exercise test, in accordance with a second preferred embodiment of the present invention.

Reference is now made to FIG. 3 which is a graphical representation of a two-dimensional matrix, corresponding to electrical potential levels of QRS complexes of a patient during an 18-minute exercise test, in accordance with a second preferred embodiment of the present invention. The graphical representation is based on a grayscale, color scale, or any other visual scale varying over the whole range of values in the matrix. The events corresponding to each column of the matrix, i.e. each vertical column in the graphical representation of FIG. 3, are morphologically aligned QRS complexes (such as shown previously in FIG. 2) extracted from a patient's standard ECG.

The axes in the current figure represent; time along exercise test 310 (10 second units), time along QRS complex 320 (msec), and amplitude 330 (mV). The amplitude axis 330 is further indicated as a color-coded scale. In the color scale of the present figure, the QRS complex itself can be easily detected between the two thin cyan strips 340 corresponding to the onset and to the offset of the QRS at about rows 45 and 125 respectively, while the red strip 350 in the middle of the figure represents a peak of the R-wave. The two large turquoise strips 360 at the beginning and at the end of each column represent the end of the P-R and the beginning of the S-T intervals, respectively.

Analysis of the two-dimensional graphical representation immediately reveals the following observations:

A significant decrease of the QRS complex amplitude during exercise, represented by a transition from the dark red color corresponding to R-wave peak 350 in the beginning of the test to an orange-yellow shade 355 at the time of peak exercise;

A significant prolongation of the QRS complex during exercise corresponds to the growing distance between the two above-mentioned cyan strips 340; and A block in the conductive system of the heart at peak exercise is a probable cause of the large and deep notch, corresponding to the yellow-green-orange pattern 370 seen between x-axis points 40 and 70.

As previously noted, inspection of HF ECG calls for solution of problems posed due to the fact that an HF ECG signal is significantly weaker than a standard ECG and that an HF ECG signal is susceptible to drastic and sudden changes, not necessarily due to an ischemic condition of the heart. Providing a global overview of the evolution of an HF ECG during a complete exercise test solves these problems:

as noise is assumed not to correlate with an HF ECG signal, its effect is likely to change from one heart beat to another. Viewing a large number of beats at a glance helps to sort out an undistorted pattern of the HF ECG and to eliminate an effect of noise; and drastic sudden changes will differ from continuous gradual ones in any global representation of the set of events, thus pointing out the correct reference signal and sorting out artificial changes not related to the heart, as noted above.

Figure 4:
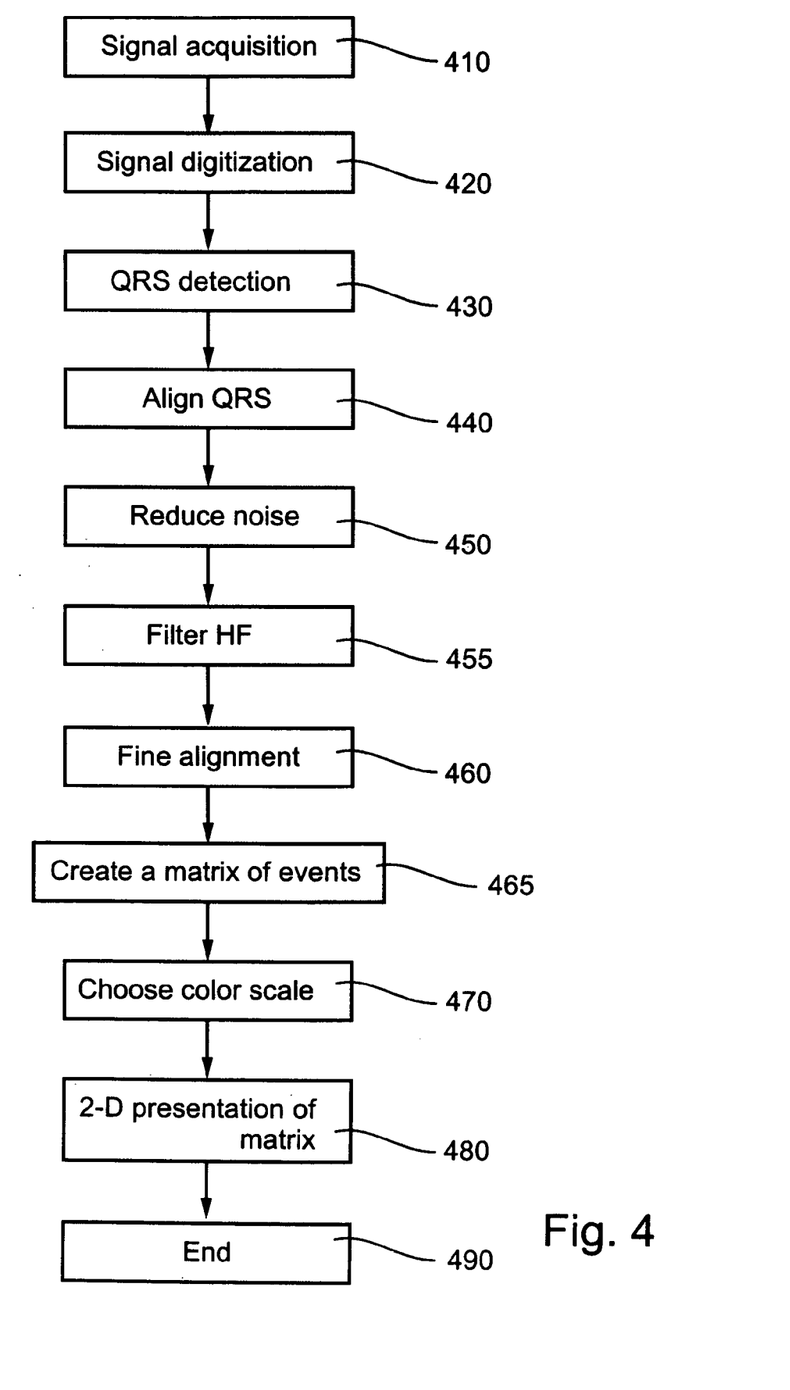
FIG. 4 is a simplified flowchart summarizing a method for efficient representation of an HF ECG signal in accordance with a third preferred embodiment of the current invention.

Reference is now made to FIG. 4 which is a simplified flowchart summarizing a method for efficient representation of an HF ECG signal in accordance with a third preferred embodiment of the current invention. Before describing the overall structure of the current figure, it is noted that none of the stages of the current figure need to deal with any significant amount of raw data at a time. Therefore, the current flowchart should be regarded as including any additional means for data storage for each stage to enable both on line and off line implementation.

Signal acquisition 410 may be preferably done by placing electrodes on an individual's skin, thus acquiring a standard ECG signal. Signal digitization 420 is accomplished by preferably digitizing the acquired signal with any A/D converter with an appropriate sampling rate (i.e. greater than twice the highest frequency of the signal to be analyzed). Note that signal digitization 420 typically also includes signal amplification prior to digitization. This step is followed by detection of a QRS segment of the signal 430. Any standard QRS detection algorithm may be used, however, attention must be given to the signal sampling rate and the frequency range being analyzed, as further discussed below.

The method for QRS detection 430 provides an output which serves as a first approximation for aligning QRS 440. QRS alignment is more finely tuned by an alignment algorithm, to be discussed below.

Note that alignment of QRS 440 appears in the flowchart before filter HF 455; meaning alignment is performed over low frequency QRS complexes. This is due to the fact that, in general, the signal to noise ratio in the HF band obviates effective signal processing. (Note that since QRS is considered to highly correlate with HF QRS, alignment of a low frequency signal will directly yield alignment of an HF signal.)

Noise reduction 450, following align QRS 440, is applied to increase the signal to noise ratio. Then, filtering of the HF signal 455 follows and a fine alignment 460 is performed. Considerations for alignment 440, noise reduction 450, HF filtering 455, and fine alignment, all of which may be interrelated, are further described below. At this point, an array of digitized waves, which has been filtered to the frequency band of interest and aligned to an adequate value, is ordered into a matrix of events 465. A color scale is chosen 470, to reflect desired relative emphases of amplitude values of the respective QRS complexes in the context of the representation of the matrix. The color scale is applied, and a 2-D presentation of the matrix 480 is produced.

Note that in QRS detection 430 any standard algorithm may be used. One commonly used algorithm consists of creating a template QRS complex (for example, by manually selecting one of the complexes in the raw data), cross correlating it with the digitized signal, and obtaining a cross correlation function. Local maxima of that function having a value exceeding a predetermined threshold may correspond to QRS complexes of an ECG signal (provided the threshold used is high enough). Another well known algorithm consists of locating all local maxima (or minima, depending on the polarization of the signal) of the overall signal that have a value higher or lower than a predetermined value corresponding to an expected level of the QRS amplitude.

Alignment of QRS 440 complexes obtained will depend highly upon: a sampling rate of the A/D converter, which determines basic time units in which the data is given (e.g. a basic time unit of 1 ms corresponds to a sampling rate 1 KHz); frequency-range of the signal to be analyzed determining the required accuracy level of the alignment algorithm (e.g. an inaccuracy level of 1 ms will not suffice for the alignment of signals of 250 Hz as it corresponds to a 90° phase shift at that frequency); and the method for QRS detection 430 whose output provides a first approximation for the alignment algorithm.

It is noted that detection algorithms might, at best, be used to align a set of events to an accuracy level on the order of magnitude of the basic time unit determined by the A/D converter. It may be assumed in most cases that a sub-sampling accuracy will be needed. Thus in general, the results of the QRS detection 430 algorithm are used as a first approximation. Results are subsequently more finely tuned by the QRS alignment 440 algorithm.

Noise reduction 450 is one of the most widely used procedures in signal processing, ranging over a large number of algorithms and techniques. A noise reduction process commonly used in ECG analysis is that of averaging a number, n, of ECG cycles over a time period resulting in an averaged signal with a noise level reduced by factor $\sqrt{n}$, relative to the level of the original signal. It should be noted, however, that this procedure tends to attenuate transient changes appearing in a number of ECG cycles of the same order as n (the number of averaged cycles). Thus, when using an averaging process, some preliminary assumption should be made concerning the expected duration of significant changes sought in the current analysis.

Design of filter HF 455 for the processed, noise reduced standard ECG QRS complexes obtained from the previous stages preferably takes into account several filter parameters including: the locality of the phenomenon in the time domain (i.e.: in looking for a given phenomenon in the QRS complex—either in a standard ECG or a HF ECG—what is the coarsest time resolution in which the given phenomenon may still be detected.); and the locality of the phenomenon in the spectrum domain (i.e. some of the most important phenomena occurring in an HF ECG do not have any trace in a standard ECG.) As the energy levels of the ECG signal in the lower band of the spectrum are much higher, another consideration is what is the largest frequency range in which a low frequency signal will not cover the above-mentioned phenomena.

Because the above-mentioned filters parameters are sometimes mutually exclusive, an optimal filter will usually depend heavily on the traits of the phenomenon to be dealt with. It should be stressed that different implementations of the algorithm, based upon a user's preference in performing analysis, may call for different filters and different frequency bands to be analyzed. These parameters should, of course, relate to the data that is to be extracted from the signal.

Note that while both noise reduction 450 and filtering HF 455 take into account time related considerations, the time related phenomena appearing at each of these steps are not interrelated, and that they relate to different time axes of the 2-D presentation 480. Indeed, while the locality of the phenomenon in the time domain—discussed in the last paragraph—deals with the problem of locating a transient phenomenon in any given QRS complex, the expected duration of the change—noise reduction 450—deals with the question of the expected number of QRS complexes to be affected by a given phenomenon.

In many cases no correlation can be found between changes in the standard ECG and the HF ECG, as mentioned above. (In fact, the superiority of the HF ECG signal over the standard ECG signal as a diagnostic aid is due to phenomena related to this point.) In some cases this situation acts as a double-edged sword since the alignment process of QRS complexes is done over the standard ECG signal, and this alignment process can be affected by local changes of the standard ECG signal which don't necessarily affect the HF signal. For this reason it is apparent that in some cases an iterated application of an alignment algorithm over small neighborhoods about the reference points obtained in align QRS 440, using HF QRS waves (and standard QRS complexes as done previously) may improve results of the first alignment.

In another approach, tackling discrepancies of an alignment of an LF signal with that of an HF can be performed at an earlier stage, avoiding the fine alignment 460, as described below.

Figure 5:
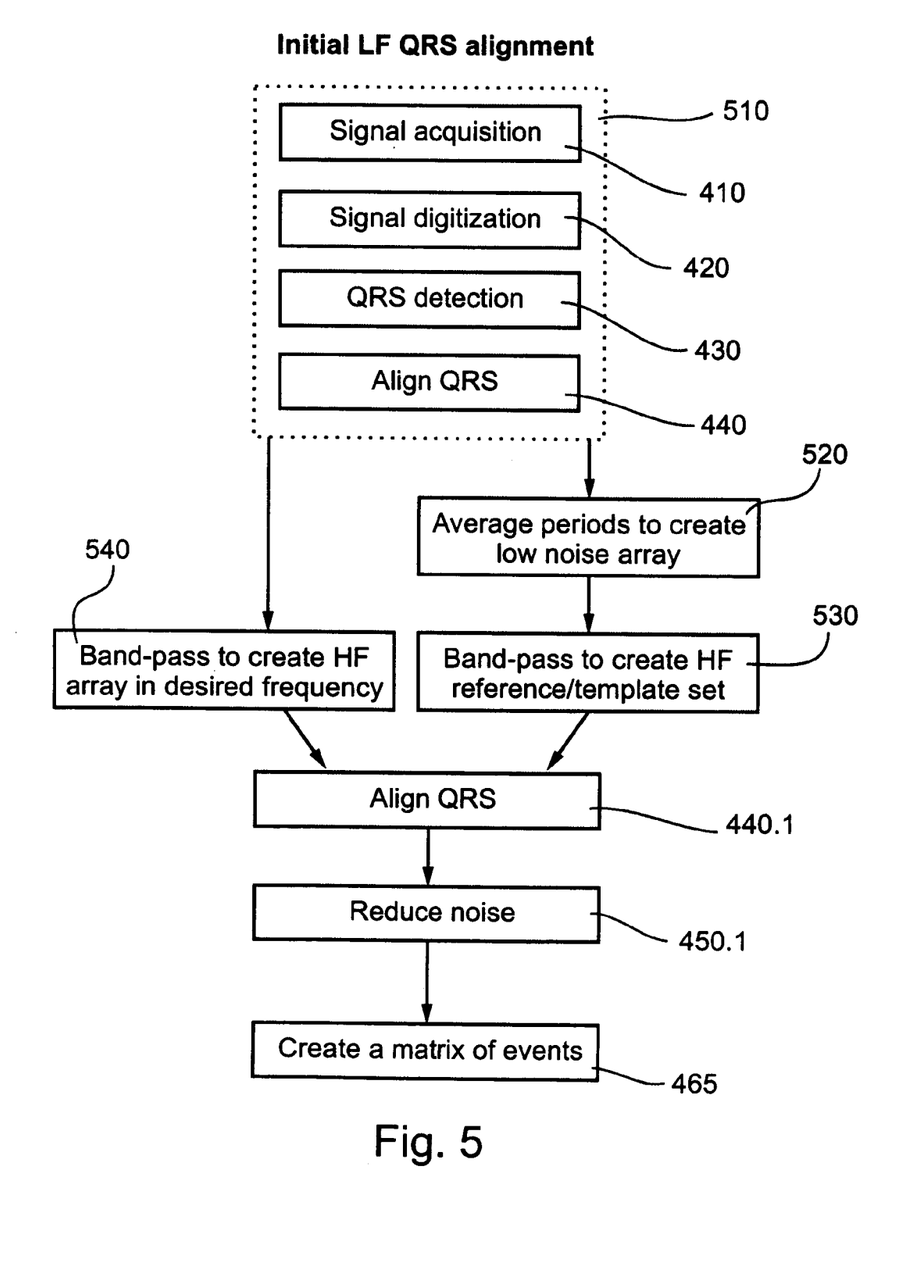
FIG. 5 is a simplified flowchart of an alternate method to obviate fine alignment in efficient representation of an HF ECG signal in accordance with a fourth preferred embodiment of the current invention.

Reference is now made to FIG. 5 which is a simplified flowchart of an alternate method to obviate fine alignment in efficient representation of an HF ECG signal in accordance with a fourth preferred embodiment of the current invention. Steps that are the same as those in previous figures are given the same reference numerals and are not described again except as necessary for an understanding of the present embodiment.

Proceed with signal acquisition 410, signal digitization 420, QRS detection 430, and align QRS 440 in similar fashion as described for FIG. 4, to create an array of aligned low frequency QRS complexes. This group of steps is initial LF QRS align 510 in the present figure. Use the aligned periods to create an array of waves with a relatively low level of noise in the frequency band of interest. This can be done as described in reduce noise 450 in FIG. 4, or more simply by averaging a predetermined number of consecutive periods in the array with relatively low level of noise in the frequency band of interest 520. Band-pass filter each of the periods previously obtained at a desired frequency range to create a set of reference/template HF periods 530. Band-pass filter each of the periods created from initial LF QRS align 510 at a desired frequency range to create an array of HF waves 540. Proceed with align QRS 440.1, followed by reduce noise 450.1 (both as previously described in FIG. 4 as QRS 440 and reduce noise 450, respectively). Use the present array of HF waves (obtained from create array of HF waves 540) as input to align QRS 440.1 and with the array of averaged and band-passed waves (obtained from create a set of reference/template HF periods 530) as a template for align QRS 440.1.

Restricting application of the alignment procedure in the present figure to one period at a time makes it possible to align periods with relatively high S/N ratio. This is because each segment to be examined actually contains a QRS complex and only one such complex. Furthermore, a cross-correlation function of the LF signals (calculated in initial LF QRS align 510) yields a good indication of where a reference point, such as that used in the previous discussion of FIG. 2 regarding time oriented alignment.

However, as the S/N ratio in the HF band is much lower than in the standard ECG, it is possible that the S/N ratio in the HF band will not allow alignment in the HF band, even as described above—while alignment may be achieved in the standard ECG. Therefore, in order to implement the modified algorithm described above, an assumption regarding the S/N ratio in the HF band, such as that previously noted regarding noise in the HF versus LF band, should be made so that the alignment procedure could be considered accurate enough.

Irrespective of which method is applied in the previous stages (i.e. according to the embodiments described in FIG. 4 or described in FIG. 5) it may now be assumed that an array of digitized periods filtered to the frequency band of interest and aligned up to an adequate level has been obtained. Sorting the array time-wise (i.e. so that periods corresponding to earlier parts of the signal appear earlier in the array, etc) and viewing it as a matrix, where each column represents a single period, the period alignment now assures that each row in the matrix represents the evolution of the portion of the QRS signal corresponding to that point over a whole time period. A graphical representation of the matrix provides a tool where changes in a signal recorded over a relatively long time may be detected at a glance.

Returning to FIG. 4, the steps "choose color scale 470" and "2-D presentation of matrix 480" are applicable in exactly the same way not only to the matrix of events in the step "create a matrix of events 465", but are applicable to any matrix of values derived from the matrix of events following mathematical manipulations (such as band-pass filtering, integration, differentiation etc.) of the columns. The step "choose color scale 470" depends heavily on signal parameters such as dynamic range and frequency of the components of the period (compared to the sampling rate). In the case of HF ECG, frequency plays an important role in the choice of the color scale.

Frequency is also directly related to another preferred embodiment of the current invention, as described below. Because the sampling rate of an A/D converter is typically 2–3 times that of the significant frequencies of the HF ECG, the difference between two neighboring samples (within the same period) may typically be on the order of the entire dynamic range of the signal amplitude. This means that a 2-D presentation of the HF signal without further processing, may result in a highly discontinuous picture with questionable value.

Two solutions to the problem noted above are:
1. increase each period's data (e.g. using interpolation filters) to obtain a subsample interpolation up to a desired level sufficient to ensure a smoother picture. This method is actually applicable because the sampling rate is assumed to be adequate, so that accurate interpolation is feasible, and because increasing each period's data may be effected in a way that assures that the data resolution increases while the dynamic range of the signal does not change (e.g. using a normalized interpolation filter); and
2. reduce the signal to a smoother signal, e.g. by presenting the signal envelope, the signal absolute value envelope etc.

The two approaches noted above represent two mutually exclusive solutions to the problem. The first solution adds redundant information and thus reduces the rate of change from bit to bit. The second solution eliminates possibly redundant information to achieve the same result of period smoothing.

Figure 6:
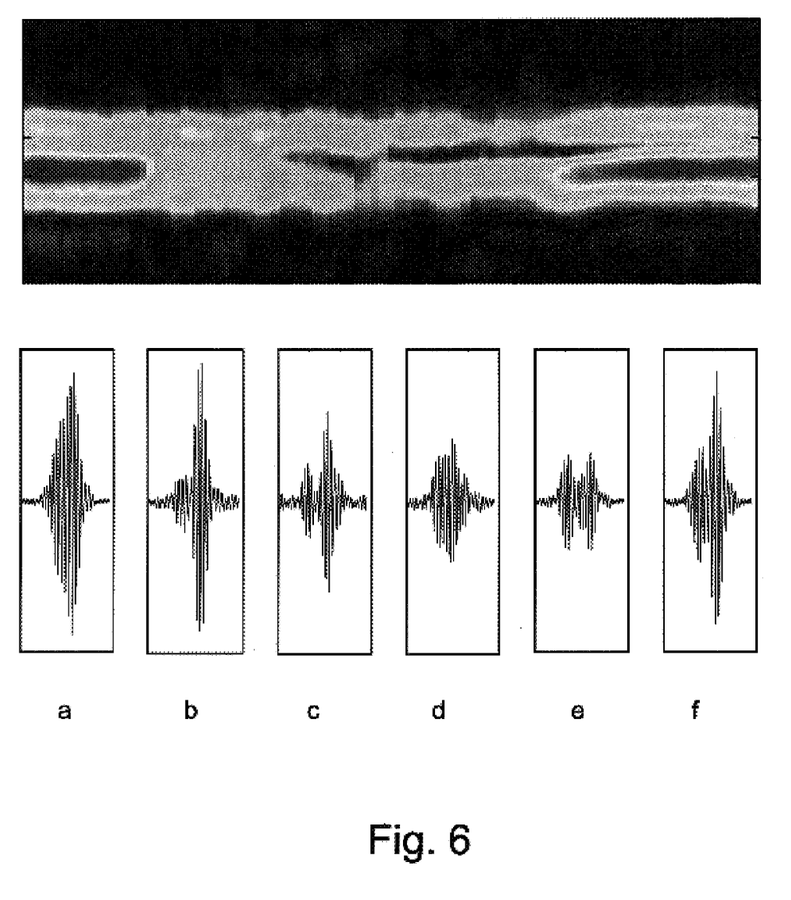
FIG. 6 is a schematic representation of a 2-D presentation of a HF QRS signal during a complete exercise test, accompanied by HF QRS signals at various stages of exercise, both according to the preferred embodiments as described in FIG. 4 and FIG. 5.

Reference is now made to FIG. 6 which is a schematic representation of a 2-D presentation of a HF QRS signal during a complete exercise test, accompanied by six HF QRS signals at various stages of exercise, both according to the preferred embodiments as described in FIG. 4 and FIG. 5.

An envelope of the absolute value of a signal in the 2-D presentation of FIG. 6 is represented as follows: Each line in the vertical axis represents a single QRS complex, whose upper part corresponds to the onset of the QRS and its lower part corresponds to the QRS offset. The hotter color shades represent higher amplitudes. The evolution of the six HF QRS signals a, b, c, d, e, and f, at various stages of exercise, may be perceived in the 2-D presentation above them. HF QRS signal "a" corresponds to the very beginning of the test, where one skilled in the art may easily detect a significant red strip preceded by an almost continuous yellow zone (vertically) which represents the approximate continuous increase in the signal's envelope. The drastic change in amplitude of the whole signal, as observed between images b and c as well as between images e and f, corresponds to a disappearance and reappearance of the red strip. Further subtler changes in the signal (such as its division to two peaks or other features of the signal) may be easily detected in the 2-D figure as well.

As specific application of the 2-D presentation method may be used for analysis of data gathered during Holter recordings, where a patient carries a small box that records his ECG continuously for 24 hours or more and the recording is played back at a later time for analysis. Holter recordings are very long signals and their use calls for an efficient presentation and analysis system that may enable inspection of the data, so that no significant information is lost, at a reasonable speed. A 2-D presentation of the signal as described in the preferred embodiments gives a user a means to inspect relatively long time intervals in the signal at a glance, effectively reducing the time required for signal inspection and making the 2-D presentation useful for Holter recordings analyses—further described below. Moreover, features of the analysis system, which is applicable to Holter analysis as well as to other periodic or nearly periodic signals, make the preferred embodiment even more useful when dealing with very long signals.

A useful application of the preferred embodiments is their integration into personal digital assistant (PDA) or like devices containing ECG signal acquisition, amplification, and digitization units. Due to their relatively small size and their graphical display, PDA-based ECG devices are much better equipped for a 2-D presentation of the signal than for the conventional 1-D method. Moreover, as is noted below, a 2-D signal representation suggests a highly compressible data structure for storage and processing of an ECG signal. Effective data compression compatible with the present invention is of importance whenever storage space is limited (e.g. portable ECG devices) or whenever on-line data transfer is required (e.g. telemedicine).

In specific applications such as Holter recordings, analysis of very long signals containing many thousands or even hundreds of thousands of waves may be required. In these cases, presentation of the whole matrix at a time may be too detailed to enable a initial global overview to locate parts of the signal that demand closer attention. In many such cases a smaller, representative matrix may be created from the original huge matrix, and the representative matrix may be analyzed using the 2-D presentation, as described above.

Creation of the representative matrix depends upon the phenomena being viewed in the signal. For example, if the expected number of appearances of a phenomenon in the wave is of interest, or if the phenomenon is not highly transient, the original matrix may be diluted by presenting every $n^{th}$ column for a predetermined value n. Alternately, if the phenomenon is expected not to change significantly from one wave to the next, averaging n columns to create a new representative column is appropriate. Finally, if a relatively short term or even transient change in the wave over time is of interest, the original matrix may be diluted so that a (n+1) column in the representative matrix is the first column in the original matrix that differs sufficiently from the (already chosen) n column. In this case, if columns of the original matrix are indexed by the numbers 1 . . . n, choose a subsequence $k_1 \ldots k_m$ such that $k_j < k_{j+1}$ for all j and such that for all j and all $k_j < t < k_{j+1}$, the t column of the original matrix does not differ sufficiently from the $k_j$ column.

In reviewing the details of the preferred embodiment described above, it will be apparent to one skilled in the art that the same methods can be applied for the analysis not only of the HF components of the QRS segment of the ECG but to any other portion of the signal (standard or HF).

In a preferred embodiment of the present invention the 2-D presentation of the signal will indeed serve as a diagnostic aid that, in cases where standard diagnostic aids are used, will help focus a user's attention to those points where abnormalities do occur, and will further supply a means to apply any other diagnostic tool for analysis of the phenomena at these points. For example, a 2D representation of the evolution of an ST segment of a signal during an exercise test will immediately reveal any abnormalities (such as ST elevation or ST depression) as well as a positive assessment of the significance of the phenomenon (e.g. the actual depth of the depression). In order to examine the phenomenon more closely using standard tools a user may be supplied with an interface, with which he may specify a region of interest in the 2-D picture, for which a standard ECG representation may automatically appear.

Thus, in a preferred embodiment the user may be supplied with a, preferably graphic interface that will enable:
Manipulation of the 2-D picture; for example, when inspecting a 2-D representation of a complete heart cycle—i.e. P-QRS-T-U-P—the QRS portion will usually dominate the color scale. Therefore a change of the color scale may be needed to inspect, for example, an ST segment more closely.
Other options may include:
change of scale of either axis of the picture;
addition/removal of markers, arrows, textual notes and other aids;

addition/removal of grids of different affinities;

transition from a 2-color representation to a standard 3-D representation;

addition/removal of indications of phenomena undetectable (or not clear enough) in a 2-D representation (such as indications of cardiac arrhythmias or exact QRS onset/offset); and zooming in to view points or regions of interest in a 2-D presentation in greater detail. These regions may correspond to a specific time period (that is, a set of successive columns in the matrix) or to a specific portion of the signal (such as the peak of a QRS complex, corresponding to a set of successive rows in the matrix) or to any combination of the above.

It should be stressed that both zooming in and the change of scale options relate to two different processes described below.

The first process corresponds only to the (graphical) presentation of the matrix. Examples are: changing the color scale by adding colors; changing linear scaling with a logarithmic one; or simply zooming into a segment of the picture using standard image processing.

The second process corresponds to the analysis of very long signals, and to the manipulation of representative matrices as previously described. In theses cases, change of scale or zooming in operations may actually add information contained in the original matrix, but not contained in the representative matrix. Obviously, whenever the second process may be applied all of the options of the first one may be available as well.

Further options may include:

direct access to standard diagnostic aids: transition to and from a region specified by the user in the 2-D presentation to a standard ECG signal presentation, these standard diagnostic aids supplied with a complete toolbox for the analysis of standard ECG signals. As noted above, the region of interest may correspond either to a continuous segment in the standard 1-D representation or to a set of discrete segments in the signal (such as a set of successive ST segments, for example) or to any combination thereof;

comparative aids, such as: evaluating changes in the 2-D presentation of a series of tests acquired over relatively long periods of time (hours, days, weeks and even years); evaluation of a single period, or a set of periods, extracted from the 2-D presentation against another signal corresponding to the same point in time (for example, if the 2-D presentation showed a HF QRS, a user may be able to compare a set of HF periods with the corresponding standard ECG periods); and comparison of a set of periods extracted from the 2-D presentation with the periods themselves. The comparison may be done either by plotting the periods one over the other in a single figure (accentuating the differences between those periods) or by plotting the periods each in a different figure (providing a more accurate overview of each period).

More generally the 2-D presentation should be regarded as a new and concise representation of periodic or almost periodic signals over relatively long periods of time. The 2-D presentation is constructed in a way that relates each of its points to the area in the original signal, which it represents. Thus no data is lost and the user may easily and continually interchange the 2-D presentation of any part of the picture with the standard continuous representation of those portions of the signal it represents.

It should be noted that the matrix of periods constructed as a basis for the 2-D presentation contains all (or at least, most) of the relevant information contained in the signal. Thus restricting analysis of the signal to that matrix does not degrade analysis results. At the same time, conciseness of the 2-D presentation may be very effective in applications of preferred embodiments, such as the above mentioned PDA ECG or other portable devices requiring transfer or storage of large quantities of periodic or almost periodic signals. Moreover, alignment of the matrix of periods assures that a difference between any two consecutive periods is minimal, and therefore the matrix data may be easily and effectively compressed (e.g. by keeping track only of the changes from one period to the next) without any loss of information.

Moreover, the 2-D presentation discussed herein is applicable to any periodic and semi-periodic signal. Issues of noise reduction and choice of frequencies to filter have been discussed above with respect to a specific example of HF ECG. Those skilled in the art will see from the above discussion how to apply these and similar issues to other types of signals.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub combination.

It will be appreciated by persons skilled in the art that the present invention is not limited to what has been particularly shown and described hereinabove. Rather the scope of the present invention is defined by the appended claims and includes both combinations and sub combinations of the various features described hereinabove as well as variations and modifications thereof which would occur to persons skilled in the art upon reading the foregoing description.

The invention claimed is:

1. Apparatus for graphically representing a substantially periodic signal having substantially periodic segments, the apparatus comprising:

a graphic encoder for converting said periodic segments into encodings respectively of properties thereof for arrangement in a single first dimension, and an indexer, associated with said graphic encoder, for successively indexing said encodings to show a succession of said segments over a second dimension, thereby to represent, within said two dimensions, dynamic changes of said properties of said periodic segments over said signal.

2. Apparatus according to claim 1, further comprising a period identifier, associated with said graphic transformer, for identifying a period of said signal, thereby to enable segmentation of said signal into said periodic segments.

3. Apparatus according to claim 2, wherein said period identifier comprises a time-oriented aligner and a morphology-oriented aligner to allow substantial alignment of said periodic segments.

4. Apparatus according to claim 3, wherein said time oriented aligner is operable to effect said alignment by defining a reference point in each of a plurality of said periodic segments.

5. Apparatus according to claim 3, wherein said morphology oriented aligner is operable to effect said alignment against a segment template.

6. Apparatus according to claim 5, wherein said segment template is at least one chosen from a list comprising: a set of local maxima and minima of said periodic segment, a characteristic overall shape of said periodic segment, and a characteristic portion of said periodic segment.

7. Apparatus according to claim 3, wherein said time-orientated aligner and said morphology-oriented aligner are operable together to effect alignment of said periodic segments.

8. Apparatus according to claim 3, wherein said time-orientated aligner is operable to effect alignment of said periodic segments.

9. Apparatus according to claim 3, wherein said morphology-orientated aligner is operable to effect alignment of said periodic segments.

10. Apparatus according to claim 1, wherein said periodic segment comprises a complex of features and wherein said graphic transformer is associated with a feature encoder for encoding a feature of said periodic segment into said encoding.

11. Apparatus according to claim 10, wherein said encoding comprises a color scale used against a relative position within said period, thereby to form said encoding as a continuous colored line representing said feature at respective positions of said periodic segment.

12. Apparatus according to claim 10, wherein said encoding comprises a gray scale used against a relative position within said period, thereby to form said encoding as a continuous gray scale line representing said at least one feature at respective positions of said period.

13. Apparatus according to claim 10, wherein said encoding comprises a gray scale used against a relative position within said period, thereby to form said encoding as a continuous gray scale contour map.

14. Apparatus according to claim 10, wherein said graphic transformer further comprises a segment smoother operable in association with said feature encoder to effect smoothing of data within said periodic segment.

15. Apparatus according to claim 10, wherein said feature is amplitude.

16. Apparatus according to claim 14, wherein said segment smoother comprises an interpolation filter and a signal data reducer.

17. Apparatus according to claim 16, wherein said interpolation filter is operable to selectively interpolate data of regions of respective periodic segments to enable a smooth representation of said data.

18. Apparatus according to claim 16, wherein said signal data reducer is operable to selectively reduce data of regions of respective periodic segments to enable a smooth representation of said data.

19. Apparatus according to claim 1, wherein said signal is a biological signal.

20. The apparatus of claim 19, wherein said signal is an ECG signal.

21. The apparatus of claim 20, wherein said ECG signal is at least one of a group comprising an exercise ECG test signal and a rest ECG signal.

22. The apparatus of claim 20, wherein said ECG signal is a Holter recording signal.

23. The apparatus of claim 3, wherein said period identifier is operable to use selected frequency band components to carry out said alignment.

24. The apparatus of claim 23, wherein said period identifier is further operable to use said selected frequency band components to improve said alignment.

25. The apparatus of claim 24, wherein said period identifier further comprises:
a noise reducer operable to reduce noise in said aligned periodic segments,
a filter for selected frequency components, said filter operable upon said aligned periodic segments following noise reduction, and
a matrix orderer operable to order said aligned periodic segments in chronological order, following said frequency filtering.

26. The apparatus of claim 23, wherein said signal is an ECG signal.

27. The apparatus of claim 24, wherein said period identifier further comprises:
a period averager, usable in association with said time-oriented aligner and said morphology-oriented aligner to provide averaging over said period segments,
a template filter for filtering over said period segments, and
an array filter for filtering over an array of segments, to further improve said alignment.

28. The apparatus of claim 27, wherein said period averager is operable to average respective periods by averaging a predetermined number of consecutive periods in said array of periodic segments having a substantially low level of noise in a frequency band of interest to create a lower noise array of periodic segments.

29. The apparatus of claim 28, wherein said template filter is operable in association with said period averager, so that said lower noise array of periodic segments is selected frequency filterable to create a template array of periodic segments.

30. The apparatus of claim 29, wherein said array filter is operable in association with said time-oriented aligner and said morphology-oriented aligner by selected frequency filtering said array of periodic segments to create a filtered array of periodic segments.

31. The apparatus of claim 30, wherein said filtered array of period segments is realignable using said template array of periodic segments as a segment template.

32. An electronic graphic representation of a periodic or semi-periodic signal, comprising:
a. a first dimension carrying a one-dimensional encoding representing properties for a periodic segment of said signal, and
b. a second dimension representing a continuation of said properties over successive segments,
thereby to form a two-dimensional coded image representative of dynamic changes within the periodicity of said signal.

33. The representation of claim 32, wherein said properties comprise a feature of said periodic segment.

34. The representation of claim 32, comprising visual encoding of said feature.

35. The representation of claim 32, comprising visual encoding of derived properties of said feature.

36. The representation of claim 32, wherein said visual encoding comprises a gray scale.

37. The representation of claim 32, wherein said visual encoding comprises a color scale.

38. The representation of claim 32, wherein said periodic signal is a biological signal.

39. The representation of claim 38, wherein said periodic signal is an ECG signal.

40. A method of representing a substantially periodic signal having substantially periodic segments to show dynamic changes in the periodicity of a signal, the method comprising:
transforming said periodic segments into single dimensional encodings of properties thereof respectively for arrangement in a first dimension and successively indexing said encodings to form a two-dimensional coded image, thereby to represent, within said image, dynamic changes of said periodic segments over said signal.

41. A method according to claim 40, further comprising identifying a period of said signal, thereby to enable segmentation of said signal into said periodic segments.

42. A method according to claim 40, wherein identification of said period of said signal further comprises the steps of:
   a. aligning said periodic segments according to at least one chosen from a list of time orientation and morphology orientation; and
   b. reducing noise in said aligned periodic segments.

43. A method according to claim 41, wherein said period identification is performed using selected frequency band components to carry out said alignment.

44. A method according to claim 43, wherein said period identification of said period further comprises the steps of:
   a. filtering a selected frequency band from said noise-reduced aligned periodic segments; and
   b. ordering said filtered periodic segments in a matrix in chronological order.

45. A method according to claim 41, wherein said period identification uses said selected frequency band components to improve said aligning of said periodic segments.

46. A method according to claim 45, wherein said signal is a biological signal.

47. A method according to claim 46, wherein said signal is an ECG signal.

48. A method according to claim 47, wherein said ECG signal is obtained during at least one chosen from a list comprising exercise ECG tests and rest ECG tests.

49. A method according to claim 47, wherein signal ECG is obtained during a Holter recording.

50. A method according to claim 40, wherein at least one of a list comprised of said identifying and said transforming, takes place in a personal digital assistant-like device.

51. A method according to claim 40, wherein at least one of a list comprised of said identifying and said transforming, takes place in a portable ECG device.

52. A method according to claim 40, further comprising manipulating said two-dimensional image graphically.

53. A method according to claim 52, wherein said manipulation comprises at least one chosen from a list comprising zoom in and zoom out.

54. A method according to claim 40, wherein said two-dimensional coded image is decodable to yield a representation of said segmented periodic segments.

55. A method according to claim 54, wherein said periodic segments are accessible by pointing on said two-dimensional image.

56. A method according to claim 40, wherein said substantially periodic signal comprises a set of signals collected from at least two non-continuous signal portions.

57. A method according to claim 55, wherein said set of signals comprises a plurality of records spanning a period of an order of magnitude within a range of seconds to years.

58. A method according to claim 56, wherein said period is of an order of magnitude reaching hours.

59. A method according to claim 56, wherein said period is within a range of orders of magnitude between hours and years.

60. A method according to claim 55, wherein said signal is a record of a biological signal comprising at least one chosen from a list comprising: EEG signals and ECG signals, wherein said signal is correlated to a series of repetitive external stimuli.

61. A method of representing a non-periodic signal containing a plurality of recurring signal segments to show dynamic changes in said signal segments, the method comprising:

transforming said signal segments into single dimensional encodings of properties of said segments respectively for arrangement in a first dimension, and successively indexing said encodings to form a two-dimensional coded image, thereby to represent, within said image, dynamic changes of said signal segments over said signal.

62. A method according to claim 60, further comprising identifying said signal segments.

63. Apparatus for analysis of a substantially periodic signal having substantially periodic segments and long-term evolution of trends appearing over a large number of said segments, the apparatus comprising:

an encoder for converting said periodic segments into encodings respectively of properties thereof, and an aligner for aligning said encodings such that corresponding properties of successive segments are aligned, thereby enabling extraction over said aligned segment encoding of parameters indicative of said long-term evolution of trends.

64. Apparatus according to claim 63, wherein said substantially periodic signal comprises high frequency information and wherein said aligner is configured to make use of properties derived at least partially from said high frequency information.

65. Apparatus according to claim 63, wherein said alignment comprises morphology oriented alignment.

66. Apparatus according to claim 63, wherein said alignment comprises time oriented alignment.

67. Apparatus according to claim 63, wherein said alignment comprises morphology oriented alignment and time oriented alignment.

* * * * *